United States Patent [19]

Leeming et al.

[11] 4,137,321

[45] Jan. 30, 1979

[54] ISOXAZOLE CARBOXAMIDES OF m-AMINOTETRAMISOLE AS ANTHELMINTICS

[75] Inventors: Michael R. G. Leeming, Canterbury; John K. Stubbs, Deal, both of England

[73] Assignee: Pfizer Inc., New York, N.Y.

[21] Appl. No.: 834,894

[22] Filed: Sep. 20, 1977

[30] Foreign Application Priority Data

Oct. 22, 1976 [GB] United Kingdom ............... 44060/76

[51] Int. Cl.$^2$ .......................................... C07D 277/60
[52] U.S. Cl. ............................. 424/270; 260/306.7 T
[58] Field of Search ................. 260/306.7 T; 424/270

[56] References Cited

U.S. PATENT DOCUMENTS

| 3,274,209 | 9/1966 | Raeymaekers et al. ...... 260/306.7 T |
| 3,708,490 | 1/1973 | Spicer et al. ................... 260/306.7 T |
| 3,828,061 | 8/1974 | Baklein et al. ................. 260/306.7 T |
| 4,014,892 | 3/1977 | Spicer et al. ................... 260/306.7 T |

*Primary Examiner*—Nicholas S. Rizzo
*Attorney, Agent, or Firm*—Connolly and Hutz

[57] ABSTRACT

Novel isoxazole carboxamides of 6-(m-aminophenyl)-2,3,5,6-tetrahydroimidazo[2,1-b,]thiazole(m-aminotetramisole) having anthelmintic properties are disclosed.

7 Claims, No Drawings

ISOXAZOLE CARBOXAMIDES OF M-AMINOTETRAMISOLE AS ANTHELMINTICS

BACKGROUND OF THE INVENTION

This invention relates to novel isoxazole carboxamides of 6-(m-aminophenyl)-2,3,5,6-tetrahydroimidazo[2,1-b]thiazole (m-aminotetramisole), to processes for their preparation, and to their use for controlling helminths in warm-blooded animals.

British patent specification No. 1,365,515 discloses 6-amino-phenyl)-2,3,5,6-tetrahydroimidazo[2,1-b]thiazoles useful in the treatment of gastrointestinal nematodes in warm-blooded animals.

U.S. Pat. No. 3,673,205 discloses dl or 1-6-(m-aminophenyl)-2,3,5,6-tetrahydroimidazo[2,1-b]thiazole and their use as anthelmintics.

U.S. Pat. No. 3,274,209 discloses dl-2,3,5,6-tetrahydro-6-phenyl-imidazo[2,1-b]thiazole and its use as an anthelmintic.

SUMMARY OF THE INVENTION

The present invention discloses the 1- and dl (racemic)- forms of the compounds of the formula:

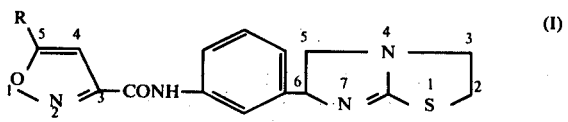

and the pharmaceutically acceptable addition salts thereof, wherein R is hydrogen or methyl.

Also disclosed is an anthelmintic composition useful for the treatment of helminth infections comprising a compound of formula (I) together with a pharmaceutically acceptable diluent or carrier.

In addition there is disclosed a method of treating helminth infections in an infected host comprising administering to said host an anthelmintic amount of a compound of formula (I).

Further disclosed is a veterinary composition comprising an anthelmintic concentration of a compound of formula (I) in an animal feed.

Typical pharmaceutically acceptable acid addition salts include the hydrochloride, hydrobromide, hydroiodide, nitrate, sulfate, acetate, lactate, tartrate and citrate salts.

R is preferably methyl.

The preferred compounds are 1- and dl-{6- m-(5-methyl-isoxazole-3-carboxamido)phenyl}-2,3,5,6-tetrahydroimidazo[2,1-b]thiazole.

We have found that the compounds of this invention are significantly more active than other closely related 6-{m-(isoxazolecarboxamido)phenyl}-2,3,5,6-tetrahydroimidazo[2,1-b]thiazoles, including the analogous 5-ethylisoxazole-3-carboxamido- and 5-phenylisoxazole-3-carboxamido- compounds, and positional isomers such as the 3-methylisoxazole-5-carboxamido compound.

The 1- forms are the most preferred forms of the compounds of the invention.

DETAILED DESCRIPTION OF THE INVENTION

The compounds may be prepared by a number of routes, including the following:

(1) The compounds may be prepared by reacting 6-(m-aminophenyl)-2,3,5,6-tetrahydroimidazo[2,1-b]thiazole (m-aminotetramisole) of the formula:

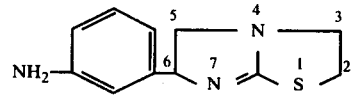

with an acid of the formula:

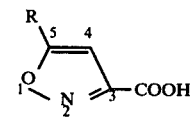

or with its functional equivalent as an acylating agent, e.g. an acid halide, "activated" ester or mixed anhydride of the compound of the formula (III).

The preferred acid halides are the acid chloride and bromide. They may be prepared by conventional procedures, e.g. by reacting the free acid with, respectively, thionyl chloride or bromide.

The preferred "activated" ester is the succinimido ester of the formula:

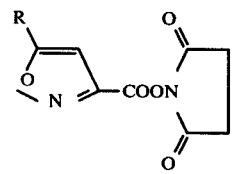

This may again be prepared by conventional procedures, e.g. by reacting the free acid with N-hydroxysuccinimide in the presence of a dehydrating agent, e.g. dicyclohexylcarboniimide. Another preferred activated ester is the phthalimido ester.

Suitable mixed anhydrides have the formula:

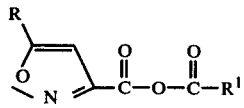

wherein $R^1$ is a $C_1-C_6$ alkyl or $C_1-C_6$ alkoxy group, most preferably a t-butyl or iso-butoxy group. They may be prepared by conventional procedures, e.g. by reacting the free acid with the appropriate alkanoyl chloride or alkyl chloroformate, respectively, e.g. pivaloyl chloride or iso-butyl chloroformate, in the presence of a base such as triethylamine.

dl-(Racemic) or 1-m-aminotetramisole should be used as the starting material according to whether the dl or l-form, respectively, of the product (I) is required. dl-m-Aminotetramisole may be resolved into its d- and l-isomers by using the method described in U.S. Pat. Nos. 3,673,205 and 3,463,786. Further, the l- form of the product (I) may be obtained by resolution of the dl-form into its dextro and laevo antipodes. For this purpose, the procedure described in British Pat. No. 1,402,689 is possible.

Although the compounds of the invention may be prepared by reacting the compound (II) with the free acid (III), it is most preferred to use the acid in the form of its acid chloride.

When the free acid form (III) is used, the reaction should generally be carried out in the presence of a dehydrating agent such as dicyclohexylcarbodiimide.

In a typical procedure involving the reaction of compound (II) with an acid chloride of compound (III), compound (II) is dissolved in an aqueous solvent, e.g. aqueous methanol, the pH lowered to e.g. 5 with dilute hydrochloride acid, the mixture cooled, and the acid chloride carefully added. After stirring the reaction mixture at room temperature for several hours, it may be acidified with dilute hydrochloric acid and washed with a suitable solvent, e.g. methylene chloride. After separation, the aqueous phase may be basified to e.g. pH 8 with a suitable base, e.g. concentrated aqueous ammonia, and extracted with a suitable solvent, e.g. methylene chloride. After separation, the organic phase may be washed with water at pH 6 to remove any unreacted m-aminotetramisole, and evaporated to dryness under reduced pressure to leave the desired product. If necessary, the product may be purified by recrystallization from a suitable solvent, e.g. acetone or ethyl acetate, or by chromatography on silica in methylene chloride containing a small amount of methanol. If the purified product is not in an acceptably crystalline form, then it may be taken up in ethanol, and excess hydrogen chloride gas passed through the ethanolic solution to convert the free base into its hydrochloride salt form. The crystalline hydrochloride may be recovered by concentrating the resulting solution under reduced pressure, and, if necessary, may be recrystallized from a suitable solvent, e.g. ethanol or isopropanol.

Alternatively, the hydrochloride salt of the product may be directly prepared in the following manner. Compound (II) is dissolved in a suitable solvent, e.g. aqueous acetone, the pH lowered to e.g. 5 with dilute hydrochloric acid, the mixture cooled, and the acid chloride of compound (III) slowly added, e.g. over a period of 30 minutes. The resulting mixture is then stirred at low temperature e.g. 10° C, for ½-1 hour, and the precipitate of the desired hydrochloride salt filtered, washed with a suitable solvent, e.g. acetone, and dried.

(2) dl-(racemic) forms of the compounds of the invention may also be prepared by cyclizing a compound of the formula:

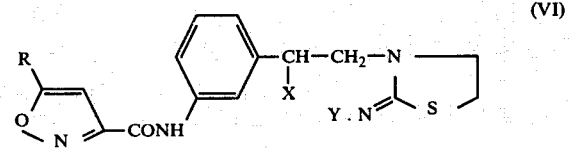

(VI)

wherein X is chlorine, bromine or hydroxy, and Y is hydrogen or $C_1$-$C_4$ alkanoyl, with the proviso that when X is hydroxy Y is hydrogen.

The preferred alkanoyl group is acetyl.

Y is preferably hydrogen.

X is preferably chlorine or bromine.

The cyclization of the compounds of the formula (VI) in which X is Cl or Br and Y is H or alkanoyl may be carried out by heating them with excess of a base which does not hydrolyze the amide linkage, e.g. aqueous potassium carbonate, aqueous triethylamine, aqueous pyridine, or dilute ammonia solution. Typical conditions are 30°-100° C for 1 to 3 hours. Typically, chloroform is present in addition to the base, the chloroform layer being separated after reaction and evaporated to dryness to yield the desired product. Again, the l-form may be prepared by resolution of the dl-product in a conventional manner.

Generally the compounds in which X is Cl or Br are prepared by the reaction of the corresponding compounds in which X is OH or $C_1$-$C_4$ alkanoyloxy with a suitable halogenating agent, e.g. thionyl chloride or bromide. It is not essential to isolate the halogenated product — this may be cyclized in situ to the desired product by reaction with the base.

The cyclization of the compounds of the formula (VI) in which X is hydroxy and Y is H may be carried out under mild dehydrating conditions. Dicyclohexylcarbodiimide is a possible dehydrating agent.

The compounds of the formula (VI) will often be obtained and cyclized in the form of their hydrochloride or hydrobromide salts.

The compounds of the formula (VI) may be prepared by methods analogous to those of the prior art. The following is a typical route:

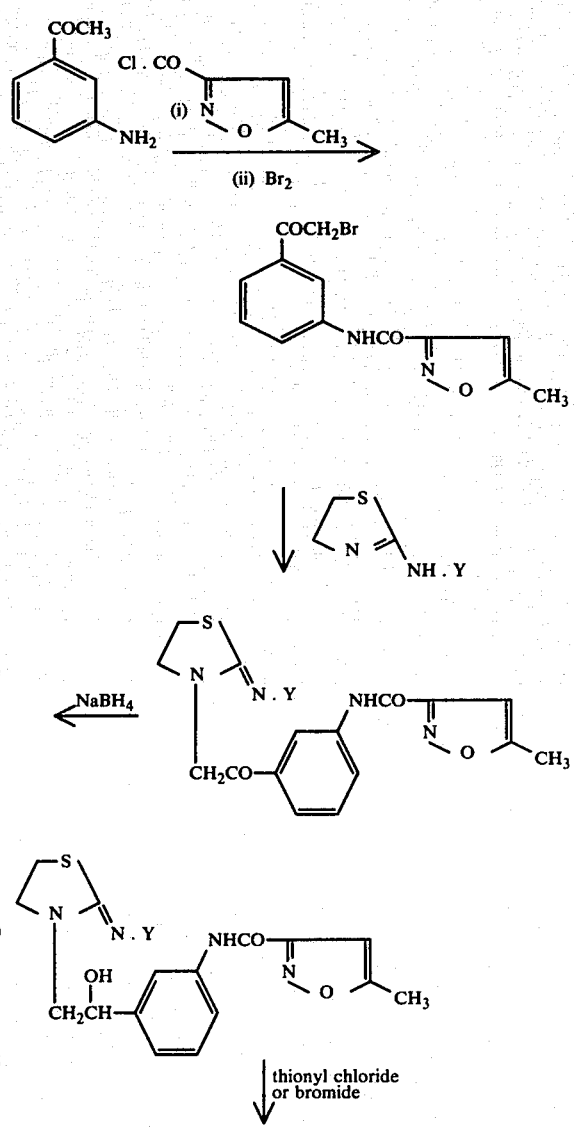

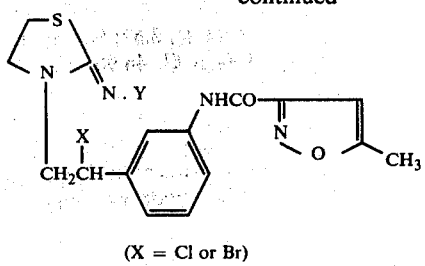

(X = Cl or Br)

(3) The pharmaceutically acceptable acid addition salts may be prepared from the corresponding free base by conventional procedures. The hydrochloride salts may for example be prepared as described in (1) above.

The compounds of the invention can be administered alone, but will generally be administered in admixture with a non-toxic diluent or carrier selected with regard to the intended route of administration. For example, they may be administered orally as aqueous solutions or in admixture with an animal feedstuff or animal feed supplement. In parenteral administration, which is preferably carried out subcutaneously or intramuscularly, the carrier may be aqueous such as water or isotonic saline or non-aqueous such as polyethylene glycol 300.

Parenteral administration of an aqueous solution is preferred, and such solutions will typically contain 1 to 20% by weight of the active compound.

Suitable dose levels are from 0.5 to 20 mg. of the active ingredient per kg. of body weight of the animal.

The compounds are also active when administered dermally, the active compound being absorbed through the skin of the animal.

The compounds of the invention are particularly active against nematodes occurring in the lungs, stomachs and intestines of sheep, cattle and other domestic animals.

The following examples, in which all temperatures are given in ° C, illustrate the invention:

EXAMPLE 1

Part A

Acid Chloride of 3-Carboxy-5-methylisoxazole

3-Carboxy-5-methylisoxazole (14.6 g) was refluxed with thionyl chloride (100 ml) for 1 hour. The reaction mixture was then evaporated to dryness under reduced pressure to remove excess thionyl chloride. Toluene was then added and the mixture again evaporated to dryness under reduced pressure to leave the crude acid chloride (16 g), which was used directly in the next stage without further purification.

Part B dl-6-{m-(5-Methylisoxazole-3-carboxamido)phenyl}-2,3,5,6-tetrahydroimidazo[2,1-b]thiazole A solution of dl-6-(m-aminophenyl)-2,3,5,6-tetrahydroimidazo[2,1-b]thiazole (1.0g) in aqueous methanol (7 ml methanol/3 ml water) acidified to pH5 with 2N hydrochloric acid was cooled to 0° and maintained at this temperature while the acid chloride prepared in Part A (1.3g) was added portionwise over a period of 10 minutes. The resulting mixture was stirred at 0° for 1 hour, and then overnight at room temperature (25°). 2N Hydrochloric acid (5 ml) was then added and the solution washed with methylene chloride. After separation, the aqueous layer was basified to pH8 by the addition of concentrated aqueous ammonia, and extracted with methylene chloride. After separation, the organic phase was washed with water at pH6 to remove any unreacted imidazo[2,1-b]thiazole starting material, dried (MgSO$_4$), and evaporated to dryness under reduced pressure to leave the desired product, dl-6-{m-(5-methylisoxazole-3-carboxamido)phenyl}-2,3,5,6-tetrahydroimidazo[2,1-b]thiazole. The product was recrystallized from acetone (yield 0.7 g, m.p. 122°-124°).

Analysis %: Found: C, 57.95; H, 4.90; N, 16.76. Required for $C_{16}H_{16}N_4O_2S$: C, 58.51; H, 4.91; N, 17.06.

Part C

Monohydrochloride salt of dl-6-{m-(5-methylisoxazole-3-carboxamido)phenyl}-2,3,5,6-tetrahydroimidazo[2,1-b]thiazole Excess hydrogen chloride gas was passed through dl-6-{m-(5-methylisoxazole-3-carboxamido)phenyl}-2,3,5,6-tetrahydroimidazo [2,1-b]thiazole (10 g, prepared as in Part B) in ethanol (150 ml), and the solution was then concentrated under reduced pressure. The desired monohydrochloride salt crystallized out of solution, and was filtered off and recrystallized from methanol (yield 9.3g, m.p. 259°-261°).

Analysis %: Found: C, 52.30; H, 4.73; N, 15.48. Calculated for $C_{16}H_{16}N_4O_2S.HCl$: C, 52.66; H, 4.69; N, 15.35.

Recrystallization of the monohydrochloride from methanol/ether (1:1) yielded the monohydrochloride monohydrate, m.p. 115°-120° (d.).

Analysis %: Found: C, 51.06; H, 5.09; H, 14.12. Calculated for $C_{16}H_{16}N_4O_2S.HCl.H_2O$: C, 50.19; H, 5.00; N, 14.63.

EXAMPLE 2 dl-6-{m-(isoxazole-3-carboxamido)phenyl}-2,3,5,6-tetrahydroimidazo[2,1-b]thiazole By a procedure similar to that of Example 1 Part B, dl-6-{m-(isoxazole-3-carboxamido)phenyl}-2,3,5,6-tetrahydroimidazo[2,1-b]thiazole, m.p. 114°-115°, was prepared from the acid chloride of 3-carboxyisoxazole and dl-6-(m-aminophenyl)-2,3,5,6-tetrahydroimidazo[2,1-b]thiazole.

Analysis %: Found: C, 57.60; H, 4.55; N, 17.19. Calculated for $C_{15}H_{14}N_4O_2S$; C, 57.32; H, 4.46; N, 17.83.

The acid chloride was prepared as in Example 1 Part A, starting from the corresponding free acid and thionyl chloride.

EXAMPLE 3

Monohydrochloride monohydrate of dl-6-{m-Isoxazole-3-carboxamido)phenyl}-2,3,5,6-tetrahydroimidazo[2,1-b]thiazole The above compound was prepared similarly to Example 1 Part C by passing excess hydrogen chloride gas through a solution of the product of Example 2 in ethanol.

Analysis %: Found: C, 48.21; H, 4.46; N, 14.95. Calculated $C_{15}H_{14}N_4O_2S.HCl.H_2O$: C, 48.85; H, 4.61; N, 15.20.

EXAMPLE 4

1-6-{m-(5-Methylisoxazole-3-carboxamido)phenyl}-2,3,5,6-tetrahydroimidazo[2,1-b]thiazole By a procedure similar to that of Example 1 Part B, 1-6-{m-(5-methylisoxazole-3-carboxamido)phenyl}-2,3,5,6-tetrahydroimidazo[2,1-b]thiazole, m.p. 120°, was prepared from the acid chloride of 3-carboxy-5-methylisoxazole and 1-6-(m-aminophenyl)-2,3,5,6-tetrahydroimidazo[2,1-b]thiazole.

Analysis %: Found: C, 57.94; H, 4.98; N, 16.78. Calculated for $C_{16}H_{16}N_4O_2S$: C, 58.52; H, 4.91; N, 17.06. Optical rotation $[\alpha]_D^{26} - 79.7°$.

EXAMPLE 5

Part A

Preparation of 3'-acetyl-5-methyl-3-isoxazolecarboxanilide.
¼ hydrate

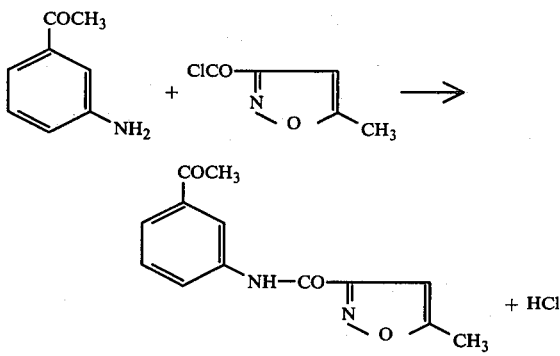

A solution of 5-methyl-3-isoxazolecarbonyl chloride (14.5 g) in acetone (30 ml) was added to a solution of m-aminoacetophenone (13.8 g) in acetone (280 ml) in the presence of anhydrous potassium carbonate (21.0 g). The mixture was stirred for ½hour, and then diluted with water. The precipitated product was filtered, washed with water and dried. Yield = 20.5 g (83%), m.p. 188°–190°.

Analysis %: Found: C, 62.77; H, 5.00; N, 10.89. Calculated for $C_{13}H_{12}N_2O_3.\frac{1}{4}H_2O$: C, 62.77; H, 5.03; N, 11.26.

Part B

Preparation of 3'-bromoacetyl-5-methyl-3-isoxazolecarboxanilide.
½ hydrate

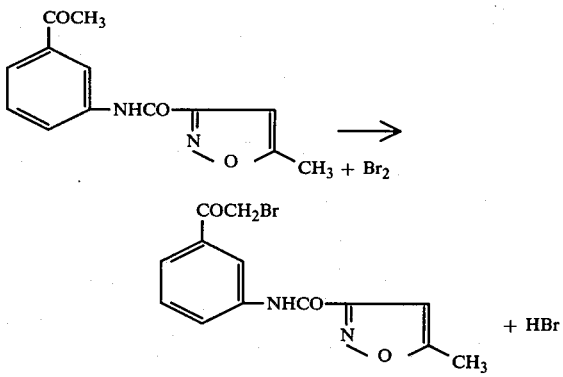

A solution of bromine (12.5 g) in chloroform (60 ml) was added to a slurry of 3'-acetyl-5-methyl-3-isoxazolecarboxanilide. ¼ hydrate (19 g) in chloroform (190 ml). The mixture was stirred for ½ hour and diluted with diethyl ether. The product was filtered and dried. Yield 21.0 g = (84%,) m.p. 172°–174°.

Analysis %: Found: C, 46.63; H, 3.57; N, 7.99. Calculated for $C_{13}H_{11}BrN_2O_3.\frac{1}{2}H_2O$: C, 46.90; H, 3.61; N, 8.43.

Part C

Preparation of 3'-[2-(2-imino-3-thiazolidinyl)acetyl]-5-methyl-3-isoxazolecarbocanilide hydrobromide

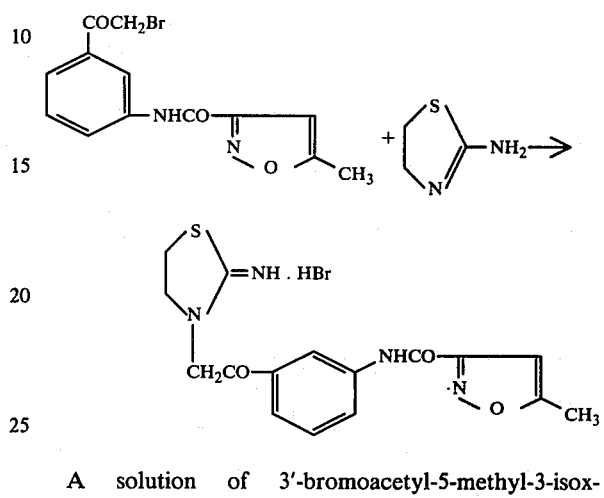

A solution of 3'-bromoacetyl-5-methyl-3-isoxazolecarboxanilide. ½ hydrate (20 g) in acetone (400 ml) was added to a stirred solution of 2-amino-2-thiazoline (6.5 g) in acetone (400 ml). The mixture was stirred for ½ hour, and the product filtered, washed with acetone and dried. Yield 25.9 g (95%), m.p. 275°–277°.

Analysis %: Found: C, 45.18; H, 4.00; N, 13.17. Calculated for $C_{16}H_{16}N_4O_3S.HBr$: C, 45.17; H, 4.13; N, 12.88.

Part D

Preparation of 3'-[1-hydroxy-2-(2-imino-3-thiazolidinyl)ethyl]-5-methyl-3-isoxazolecarboxanilide hydrochloride

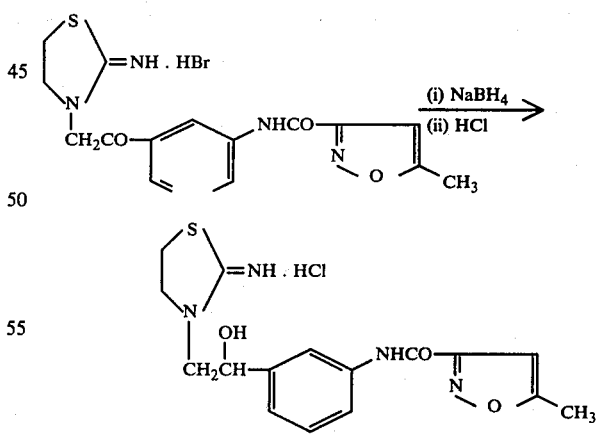

Sodium borohydride (11.5 g) was added to a stirred slurry of 3'-[2-(2-imino-3-thiazolidinyl)acetyl]-5-methyl-3-isoxazolecarboxanilide hydrobromide (23.0 g) in industrial methylated spirits (230 ml). The mixture was stirred for ½ hour, diluted with water and filtered. The crude product obtained was dissolved in acetone (240 ml) and a solution of hydrogen chloride in acetone added to it. The solid obtained was filtered, washed with acetone and dried. Yield 15.0 g (90%), m.p. 206°–208°.

Analysis %: Found: C, 50.19; H, 5.17; N, 15.04. Calculated for $C_{16}H_{18}N_4O_3S\cdot HCl$: C, 50.20; H, 4.96; N, 14.64.

Part E

Preparation of dl-6-{m-(5-methylisoxazole-3-carboxamido)phenyl}-2,3,5,6-tetrahydroimidazo[2,1-b]thiazole monohydrochloride monohydrate

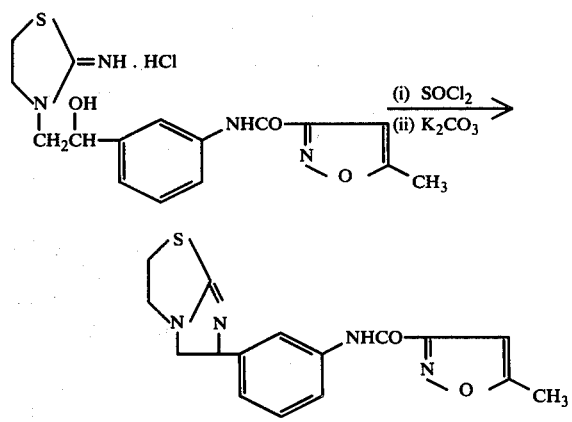

3′-[1-Hydroxy-2-(2-imino-3-thiazolidinyl)ethyl]-5-methyl-3-isoxazolecarboxanilide hydrochloride (3.8 g) was added to stirred thionyl chloride (12 ml) at 5°. The mixture was stirred at 5°–10° for ½ hour, and the solution evaporated to dryness at 25° under vacuum. The resulting residue was stirred at 60° with a mixture of chloroform and aqueous potassium carbonate solution for 1 hour. The chloroform layer was separated and evaporated to dryness. The solid obtained was dissolved in acetone (200 ml) and a solution of hydrochloric acid in acetone added to it. The product was filtered, washed with acetone and dried. Yield = 2.6 g (68%). The product was shown by n.m.r. and i.r. to be identical with the product of Example 1, Part C.

EXAMPLE 6

Preparation of dl-6-{m-(5-methylisoxazole-3-carboxamido)phenyl}-2,3,5,6-tetrahydroimidazo[2,1-b]thiazole monohydrochloride monohydrate dl-6-(m-aminophenyl)-2,3,5,6-tetrahydroimidazo[2,1-b]thiazole (14.5 g) was stirred in acetone (100 ml) and water (25 ml) and 2.5N HCl (27 ml) added to give a clear solution of pH approximately 5.

This solution was stirred and cooled to 5° and a solution of 5-methyl-3-isoxazolecarbonyl chloride (14.5 g) in acetone (30 ml) added over ½ hour at 5°–10°. The resulting mixture was stirred at 10° for ½ hour and the precipitated solid filtered, washed with acetone and dried. Yield = 21 g (87.5%), m.p. 118°–121° (d). N.M.R., I.R. and T.L.C. analyses showed the product to be identical with the product of Example 1 Part C.

EXAMPLE 7

An aqueous composition suitable for administration by injection to human or non-human animals is as follows:

| | |
|---|---|
| Monohydrochloride salt of dl-6-{m-(5-methylisoxazole-3-carboxamido)-phenyl}2,3,5,6-tetrahydroimidazo[2,1-b]thiazole | up to 10% w/v |
| Methadioxole or Polyethylene Glycol 300 | up to 50% w/v |
| Water | balance to 100% |

The composition may be prepared by mixing the ingredients together, and may be administered in one or more doses.

Obviously the amount of the active ingredient will vary according to the dose response and weight of the animal but will generally be in the range of 0.5 to 20 mg per kg. of body weight, typically 2.5 mg/kg.

EXAMPLE 8

Administration of the compounds of the invention to animals may conveniently be carried out by incorporating them into feed mixtures. The typical dose used will be 0.5 to 20 mg/kg of body weight per day, i.e. 250 mg to 10 gm per day for 500 kg. cattle. Assuming such an animal consumes 5 kg. of feed supplement per day, then the said quantity of the active material may be mixed with 5 kg. of feed supplement.

EXAMPLE 9

The activity of the compounds in a triple infection mouse screen against a concurrent infection of *Nematospiroides dubius, Syphacia obvelata* and *Hymenolepsis nana* may be determined as follows. Albino mice, 20 grams in weight, are infected and treated according to the following procedure. Taking the initial infection as day 0, mice are infected with 2,000 *H. nana* ova on day 0 and 100 *N. dubius* larvae on day 5 and then exposed to a Syphacia infected colony for 4 days. The mice are then treated with test compound in groups of four either once on day 14 or on three consecutive days 14–16 by the oral or subcutaneous route. The mice are autopsied on day 19 examined for the presence of worms. The results obtained are compared with those from an untreated infected control (12 per group). For *N. dubius* total counts are carried out and activity is expressed as a percentage reduction. Infections of the other parasites are graded, *Syphacia* (0–3) and *H. nana* (0–3) and activity is expressed by comparing group mean grades. Polyethylene glycol is the standard vehicle used in the preparation of the test compounds for dosing, although aqueous solutions are used for water-soluble substances, and materials insoluble in both polyethylene glycol and water may be ball-milled in aqueous 1% Tween 80. The mg/kg. levels used may be for example up to 12.5 mg/kg.

The activities of the compounds of the invention against the helminth *N. dubius* using the above method was found to be as follows:

| | Dose (mg/kg) | | | | | |
|---|---|---|---|---|---|---|
| Compound | 12.5 | 6.25 | 3.12 | 1.56 | 0.78 | 0.39 |
| Product of Example 1 Part B % Clearance (s.c.) Product of Examples 1 Part C, | 100% | 99% | 72% | — | — | — |

-continued

| Compound | Dose (mg/kg) | | | | | |
|---|---|---|---|---|---|---|
| | 12.5 | 6.25 | 3.12 | 1.56 | 0.78 | 0.39 |
| 5 and 6, % Clearance (s.c.) | — | 99% | 79% | 68% | — | — |
| Product of Examples 1 Part C, 5 and 6, % Clearance (oral) | — | — | 100% | 98% | 56% | 31% |
| Product of Example 2 % Clearance (s.c.) | 100% | 89% | 65% | 39% | — | — |
| Product of Example 3 % Clearance (s.c.) | 96% | 88% | 100% | — | — | — |
| Product of Example 4 % Clearance (s.c.) | 100% | 100% | 100% | — | — | — |

What is claimed is:

1. The dl- and l- forms of the compounds of the formula:

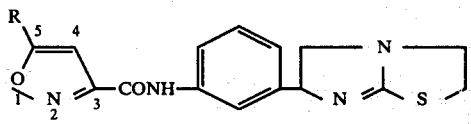

and the pharmaceutically acceptable acid addition salts thereof, wherein R is hydrogen or methyl.

2. A compound as claimed in claim 1 wherein the compound is in the form of a hydrochloride, hydrobromide, hydroiodide, nitrate, sulfate, acetate, lactate, tartrate or citrate salt.

3. 1- or dl-6-{m-(5-methylisoxazole-3-carboxamido)-phenyl}-2,3,5,6-tetrahydroimidazo[2,1-b,]thiazole, and the hydrochloride salts thereof.

4. An anthelmintic composition useful for the treatment of helminth infections comprising a compound as claimed in claim 1 together with a pharmaceutically acceptable diluent or carrier.

5. A method of treating helminth infections in an infected host comprising administering to said host an anthelmintic amount of a compound as claimed in claim 1.

6. A method as claimed in claim 5 comprising administering from about 0.5 to 20 mg. per kg. of body weight daily of said compound.

7. A veterinary composition comprising an anthelmintic concentration of a compound as claimed in claim 1 in an animal feed.

* * * * *